United States Patent [19]

Madison et al.

[11] Patent Number: 5,326,861

[45] Date of Patent: Jul. 5, 1994

[54] PREPARATION OF ORGANIC MACROCYCLIC COMPOUNDS

[75] Inventors: Stephen A. Madison, Valley Cottage, N.Y.; Jean H. Koek, Schiedam, Netherlands; Johan J. W. Eshuis, Rotterdam, Netherlands; Ronald P. Potman, Schiedam, Netherlands

[73] Assignee: Lever Brothers Company, Division of Conopco, Inc., New York, N.Y.

[21] Appl. No.: 964,243

[22] Filed: Oct. 21, 1992

[51] Int. Cl.$^5$ ............................................ C07D 255/00
[52] U.S. Cl. ................................................ 540/474
[58] Field of Search ..................................... 540/474

[56] References Cited

FOREIGN PATENT DOCUMENTS 0375333 6/1990 European Pat. Off. .
WO86/02352 4/1986 PCT Int'l Appl. .

OTHER PUBLICATIONS

Organic Synthesis, 58, pp. 86–98 (1978).
Luk'Yanenko et al, Khim Geterotsikl, Soedin., 23 (3), pp. 401–404 (1990).
Luk'Yanenko et al, Zhurnal Organ, Khimii, 25, 8, pp. 1776–1784 (Dec. 30, 1989) with English Translation, pp. 1537–1544 (Aug. 1990).
Luk'Yanenko et al, Zhurnal Organ, Khimii, 23 (3), pp. 660–662 (Jun. 3, 1986 with English Translation) pp. 598–599 (Mar. 1987).
Searle and Geue, Aust. J. Chem., 37, pp. 959–970 (1984).
Qian et al, Tetrahedron Letters, 31 (45), pp. 6469–6472 (1990).
Biernat and Luboch, Tetrahedron Letters, 40 (10), pp. 1927–1929 (1984).
Buttafava et al, Inorg. Chem., 25, pp. 1456–1461 (1999986) (1986).
McAuley et al, Inorg. Chem., 23, pp. 1938–1943 (1984).
Schneider and Busch, Chem. Ber., 119, pp. 747–750 (1986).
Bogatsky et al, Communications, pp. 136–138 (Feb. 1984).
Pilichowski et al, Tetrahedron Letters, 41 (10), at PP. 1961.

*Primary Examiner*—Mukund J. Shah
*Assistant Examiner*—P. K. Sripada
*Attorney, Agent, or Firm*—Milton L. Honig

[57] ABSTRACT

An improved process for preparing triazacyclo compounds and, in particular, 1,4,7-tritosyl-1,4,7-triazyacyclononane. The process involves reacting a diethylenetriamine triarylsulphonate with a cyclising agent selected from the group consisting of diaryl sulphonates, dialkyl sulphonates, ethylene dibromide, ethylene dichloride and diacetylglycol in the presence of ultrasound.

1 Claim, No Drawings

PREPARATION OF ORGANIC MACROCYCLIC COMPOUNDS

FIELD OF THE INVENTION

This invention relates to the preparation of triazacyclo compounds and, in particular 1,4,7-tritosyl-1,4,7-triazacyclononane.

THE RELATED ART

Triazacyclo compounds and methods for their preparation are described in the literature. For example, Richman and Atkins in *J.Am.Chem.Soc* (1974), 96, pp. 2268 describes a method for preparing 1,4,7-tritosyl-1,4,7-triazacyclononane, a compound of formula I.

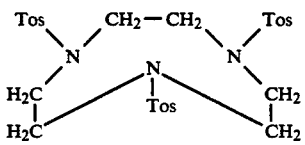

The preparation involves reacting diethylenetriaminetritosylate disodium salt with ethylene glycol ditosylate in dimethylformamide (DMF).

A major disadvantage with this route is that it uses DMF as solvent. DMF cannot readily be recycled and therefore, problems exist regarding the disposal of such a material. Furthermore, concern exists that DMF is potentially a harmful substance the use of which, if possible, should be avoided.

Yet a further disadvantage with this known method is that rate of formation of the triazacyclo species is extremely slow.

Thus this method, although suitable for laboratory scale preparation, cannot therefore readily be adopted for commercial production of triazacyclo compounds.

1,4,7-Tritosyl-1,4,7-triazacyclononane is currently of particular interest in that it be detosylated and subsequently methylated to form 1,4,7-trimethyl-1,4,7-triazacyclononane. This organic ligand may then reacted with a manganese compound in aqueous medium to form dinuclear manganese complexes for example [Mn$_2$IV ($\mu$-O) 3(Me$_4$TACN)$_2$)(PF$_6$)$_2$ as described in copending European Patent Specifications 458 397 and 458 398 or mononuclear manganese complexes as described in our copending British Patent Application No 9127060.3. Such manganese complexes are effective bleach catalysts.

SUMMARY OF THE INVENTION

The present invention seeks to provide an improved method for the preparation of triazacyclo compounds which does not require DMF as the solvent and proceeds at a more rapid rate.

Accordingly, the present invention provides a method for the preparation of triazacyclo compounds which comprises reacting i) diethylenetriamine triarylsulphonate and ii) a cyclising agent selected from diaryl sulphonates, dialkyl sulphonates, ethylene dibromide, ethylene dichloride and diacetylglycol in alkaline conditions in a reaction medium comprising an organic solvent and water, at a temperature within the range of from 45° C to a temperature less than the boiling point temperature of the reaction medium and in the presence of ultrasound.

DETAILED DESCRIPTION

The advantage of carrying out the reaction under the catalysis of ultrasound is that it is much faster than the corresponding reaction carried out in its absence.

The source of ultrasound may be provided by standard equipment, such as an ultrasound probe, operating in the range 20 to 100 KHz.

Preferably the diethylene triamine triarylsulphonate is selected from diethylenetriamine tritosylate and diethylenetriamine tribenzenesulphonate.

Particularly preferred cyclising agents include ethylene glycol ditosylates and ethylene glycol dibenzenesulphonates.

Preferably the reaction is carried out at a temperature within the range 45° to 90° C., most preferably 65° to 85° C.

A water-soluble base is added to the reaction mixture in order to achieve the alkaline conditions. Inorganic basic salts such as sodium hydroxide are preferred. Preferably the pH of the reaction mixture should be within the range 10 to 13, most preferably 11 to 12.

The organic solvent should be chosen such that the cyclising agent is soluble in the solvent. Suitable organic solvents include toluene, anisole, chlorobenzene and xylene. Most preferred are toluene and xylene because of their low toxicity.

Diethylene triamine tritosylate is preferably used in the form of a dialkli metal salt and, in particular disodium diethylene triamine tritosylate. It may be prepared according to the method described by R W Hay in *J Chem Soc Dalton Trans.*, 1441-1445 (1979).

Ethylene glycol ditosylate is prepared according to the method described by G W Kabalka in *J Org. Chem.*, 51, 2386 (1986).

A cationic phase transfer catalyst (PTC) may be added to the reaction mixture to increase the rate of reaction. A PTC usually is of the structural formula:

$$(R'')_4NX$$

wherein R" is selected from aryl, benzyl, phenyl, alkyl; and X is an anion selected from iodide, bromide, chloride, bisulphate, sulphate, phosphate and organic moieties attached to the aforementioned anions. A particularily preferred catalyst is Bu$_4$NOH.

The following non-limiting examples further illustrate the invention.

EXAMPLES

Experiments were performed using a Heat Systems Ultrasound probe (Model XL2020; 0.5 inch tip) operating at 20 KHz. The tip was immersed to a depth of about 2 cm in the reaction solution. The reaction vessel was a jacketed Rosett cooling cell (250 ml), thermostatted with a Lauda compact thermostat MS3. At timed intervals during the reaction samples were withdrawn from the reaction vessel, evaporated to dryness, dissolved in CDCl$_3$ and analysed by 1H nmr, referenced to TMS (.=0).

The conversion of ethylene glycol ditosylate (EGT) to 1,4,7-tritosyl-1,4,7--triazacyclononane (Tos$_3$TACN) was determined from the ratio of the peak areas of the EGT and Tos$_3$TACN to CH$_2$ signals at 4.2 and 3.5 ppm, respectively, using the formula conversion (%) = 100 × {(int Tos₃TACN)/(int EGT)} {3+(int TOS₃TACN)/(int EGT) } where (int Tos3TACN) and (int EGT) are the integrals of the peak areas for the nmr signals attributable to Tos3TACN and EGT respectively.

EXAMPLE 1

The reaction vessel was initially thermostated to 65° C. Thereafter, diethylenetriamine-tritosylate disodium (TaS3DET) (6.00 g; 0.010 mol), ethylene glycol ditosylate (EGT) (3.93 g ; 0.01 mol), toluene (100 ml), NaOH (20 ml of 1.16M) and Bu₄NOH (1.0 ml of 1.0M) were added to the reaction vessel. The tip of the ultrasound probe was immersed in the reaction vessel. Then the ultrasound probe was switched on and adjusted to maximum power output (30% for the solvent systems used in the experiments). The reaction was continued for 5 hours and monitored using the method described above. The results are presented in Table I below.

EXAMPLE IA

In a comparative set of experiments the reaction was carried out in the absence of a source of ultrasound waves.

Example I was repeated except the reaction vessel was provided with a reflux condenser and a stirring bar. No ultrasound probe was used. The reaction was carried out at the reflux temperature for a toluene/water azeotrope (i.e., 85° C.). It was continued for 5 hours and monitored by nmr.

The results obtained are presented in Table I.

TABLE I

| Example I Time/h | Example Ia % Conversion | |
|---|---|---|
| 0 | 0 | 0 |
| 0.5 | 7.3 | 3.5 |
| 1.0 | 15.7 | 6.0 |
| 1.5 | 21.9 | 8.5 |
| 2.0 | 28.1 | 13.8 |
| 2.5 | 33.3 | 16.0 |
| 3.0 | 39.1 | 18.5 |
| 3.5 | 44.3 | 22.8 |
| 4.0 | 48.6 | 26.7 |
| 4.5 | 51.9 | 30.4 |
| 5.0 | 55.0 | 33.9 |

The results demonstrate that the reaction carried out in the presence of ultrasound is faster than one carried out in the absence of ultrasound.

EXAMLE IB

To confirm the increase in reaction rate was due to a sonochemical effect and independent of the method of mixing an experiment was carried out in a baffled reaction vessel with a turbine overhead stirrer operating at various rpm.

To a 1.5l Jacketed reaction vessel thermostatted at 65° C. with four baffles and equipped with a reflux condenser and a Heidolph RZR50 overhead stirrer Tos3DET (40.0 g; 0.067 mol), EGT (26.2 g; 0.067 mol), NaOH (6.7 ml of 1.0M), Bu₄NOH and toluene (667 ml) was added. The reaction was continued for 5 hours and monitored by nmr.

| | Percent Conversion | | |
|---|---|---|---|
| Example Ia | | Example Ib | |
| time/h | 200 rpm | 1000 rpm | 2000 rpm |
| 0 | 0 | 0 | 0 |
| 0.5 | 3.5 | 4.1 | — | 3.8 |
| 1.0 | 6.0 | 6.2 | 5.7 | 6.3 |
| 2.0 | 13.8 | 13.5 | 14 | 12.3 |
| 4.0 | 26.7 | 25.3 | 25.0 | 24.2 |
| 5.0 | 32.1 | 32.3 | 31.3 | 32.8 |

The results show the reaction rate was independent of the method and speed of mixing.

EXAMPLE II

Example I was repeated except the power output of the ultrasound probe was reduced to 15%.

| Time/h | % Conversion |
|---|---|
| 0 | 0 |
| 0.5 | 4.3 |
| 1.0 | 9.2 |
| 2.0 | 17.4 |
| 3.0 | 23.9 |
| 4.0 | 29.6 |
| 5.0 | 34.7 |

These results, when compared with the results of Example I, demonstrate the increase in reaction rate observed is dependent on the power output of the ultrasound source.

EXAMPLE III

Example I was repeated except toluene was replaced by a range of solvents. The following results were obtained:

| | ORGANIC SOLVENT | | | | |
|---|---|---|---|---|---|
| | A | B | C | D | E |
| time/h | % conversion | | | | |
| 0 | 0 | 0 | 0 | 0 | 0 |
| 1.0 | 15.7 | 13.1 | 9.7 | 14.2 | 0.4 |
| 2.0 | 28.1 | 30.3 | 25.3 | 27.4 | 0.6 |
| 3.0 | 39.1 | 35.1 | 32.7 | 37.1 | 0.6 |
| 4.0 | 48.6 | 47.5 | 43.7 | 46.5 | 0.7 |
| 5.0 | 55.0 | 56.9 | 53.2 | 54.1 | 0.7 | a—toluene; b—anisole; c—chlorobenzene; d—xylene; e—ditertiarybutylether.

With the exception of ditertiarybutylether, the % conversion was independent of the solvent used. The low conversion for ditertiarybutylether can be attributed to the insolubility of EGT in this solvent.

EXAMPLE IV

Examples I and Ia were repeated over a range of temperatures and the difference in reaction rate (.RR) determined, where the difference is % conversion (ultrasound present—ultrasound absence) after a reaction time of 5 hours.

The following results were obtained.

| Temperature/°C. | .RR |
|---|---|
| 35 | 1.5 |
| 45 | −0.7 |
| 55 | 6.3 |
| 65 | 21.1 |

| Temperature/°C. | .RR |
| --- | --- |
| 75 | 16.8 |
| 85 | 14.8 |

The results demonstrate a temperature of about 65° C. gives optimum results.

EXAMPLE V

In this example the formation of Tos₃TACN in the presence and absence of Bu₄NOH was examined. Examples I and Ia were repeated except a temperature of 85° C. was used.

The following results were obtained.

| Time/h | Conditions | | |
| --- | --- | --- | --- |
| | f | g | h |
| 0 | 0 | 0 | 0 |
| 0.5 | 12.7 | 2.5 | 0.5 |
| 1.0 | 27.2 | 4.3 | 1.2 |
| 1.5 | 37.0 | 12.4 | 1.4 |
| 2.0 | 46.9 | 28.6 | 2.1 |
| 3.0 | 56.8 | 48.0 | 3.4 |
| 4.0 | 68.3 | 63.0 | 5.4 |
| 5.0 | 73.0 | 73.2 | 6.1 |

Conditions
f—with ultrasound + Bu₄NOH
g—with ultrasound, no Bu₄NOH
h—without ultrasound, + Bu₄NOH

We claim:
1. A method for the preparation of 1,4,7-tritosyl-1,4,7-triazacyclononane which comprises reacting
   i) diethylenetriamine tritosylate and
   ii) a cyclising agent selected from the group consisting of ethylene glycol ditosylate, ethylene glycol dibenzene sulphonate, ethylene dibromide, ethylene dichloride and diacetylglycol
under alkaline conditions in a reaction medium comprising an organic solvent wherein the cyclising agent is soluble and water, at a temperature within the range of from 45° C. to 90° C. and exposing the reaction medium to ultrasound.